United States Patent [19]

Yamauchi et al.

[11] Patent Number: 5,069,226
[45] Date of Patent: Dec. 3, 1991

[54] CATHETER GUIDEWIRE WITH PSEUDO ELASTIC SHAPE MEMORY ALLOY

[75] Inventors: Kiyoshi Yamauchi, Miyagi; Takahiro Kugo; Yasuo Miyano, both of Shizuoka, all of Japan

[73] Assignees: Tokin Corporation, Sendai; Kabushiki Kaisha Terumo, Tokyo, both of Japan

[21] Appl. No.: 515,591

[22] Filed: Apr. 27, 1990

[30] Foreign Application Priority Data

Apr. 28, 1989 [JP] Japan .................................. 1-107855
Apr. 28, 1989 [JP] Japan .................................. 1-107856
Apr. 28, 1989 [JP] Japan .................................. 1-107857

[51] Int. Cl.⁵ .............................................. A61B 5/00
[52] U.S. Cl. ...................................... 128/772; 128/657; 604/95; 604/281
[58] Field of Search ............... 128/656, 657, 658, 772; 604/93, 95, 280, 281

[56] References Cited

U.S. PATENT DOCUMENTS

| | | | |
|---|---|---|---|
| 3,753,700 | 8/1973 | Harrison et al. | 148/402 |
| 4,509,517 | 4/1985 | Zibelin | 606/127 |
| 4,665,906 | 5/1987 | Jervis | 606/78 |
| 4,813,434 | 3/1989 | Buchbinder et al. | 128/772 |
| 4,832,444 | 5/1989 | Takahashi et al. | 350/96.26 |
| 4,925,445 | 5/1990 | Sakamoto et al. | 604/95 |
| 4,969,890 | 11/1990 | Sugita et al. | 606/192 |
| 4,984,581 | 1/1991 | Stice | 128/772 |

*Primary Examiner*—Max Hindenburg
*Attorney, Agent, or Firm*—Hopgood, Calimafde, Kalil, Blaustein & Judlowe

[57] ABSTRACT

A catheter guide wire is for use in guiding of a catheter to a destination position in vessels in body and comprises a solid core wire of a Ti-Ni shape memory alloy and an outer jacket covering the core wire. In order to provide a plasticity to one end portion of the core wire, at least one end portion is made of a 45.0–51.0 at % Ni-0.5–5.0 at % Fe-Ti shape memory alloy and is heat treated at 400°–500° C. The end portion is provided with a pseudo elasticity at a temperature about 37° and a plasticity at a temperature below 80° C. Alternatively, the end portion may be made of a 50.3–52.0 at % Ni-Ti alloy and is heat treated at a temperature of 700° C. In order to improve operability of the catheter guide wire, the remaining portion other than the end portion is made of provided with a comparatively high rigidity by a usual Ti-Ni shape memory alloy which is not heat treated. Alternatively, the remaining portion is covered with an inorganic layer. The inorganic layer is a coating and alternatively is a cladding. The solid core wire is covered with a synthetic resin layer to form the catheter guide wire.

14 Claims, 2 Drawing Sheets

CATHETER GUIDEWIRE WITH PSEUDO ELASTIC SHAPE MEMORY ALLOY

BACKGROUND OF THE INVENTION

1. Field of the Invention

The present invention relates to a catheter guide wire for use in guiding a catheter, and in particular, to such a catheter guide wire using a shape memory alloy with pseudo elasticity.

2. Description of the Prior Art

The catheter guide wire is for guiding the catheter through cavities such as blood vessels within a body. The catheter guide wire is inserted into a cavity of the body and is steered therethrough so that its end arrives at a destination position. Then, the catheter is fitted onto the catheter guide wire and is guided through the blood vessel by the catheter guide wire to the destination position.

Since a blood vessel has various branches in different directions within the body, the catheter guide wire must be steerable through the blood vessels so as to reach the destination position.

It is well known in the prior art to make the catheter guide wire of a shape memory alloy so as to use pseudo elasticity of the shape memory alloy for the steerability of the wire. Reference is made to JP-A-63-171570 (Reference I), JP-A-64-49570 (Reference II) and others.

It is also known to use the shape memory alloy for the catheter itself and other medical appliances in JP-A-60-100956 based on U.S. patent application Ser. No. 541,852 filed on Oct. 14, 1983 (Reference III).

A typical shape memory alloy is Ti-Ni alloy as shown in all of the Reference. Cu-Zn-Al, Cu-Al-Ni, Fe-Mn alloys are also known as the shape memory alloy as shown in Reference I.

Those shape memory alloys may have the pseudo elasticity at a temperature of about 37° C. by controlling ingredients and their amounts of the alloy composition and/or a temperature for heat-treating the alloy.

The pseudo elasticity is characterized by a stress-strain curve having a generally rectangular hysteresis loop wherein strain gradually increases with increase of stress and rapidly and suddenly increases at an elevated stress (yield point) while strain gradually reduces with reduction of stress and rapidly and suddenly reduces at a reduced stress, as shown at 1 in FIG. 1 of Reference I, in FIG. 6 of Reference II, and in FIGS. 1 and 2 of Reference III.

Although the catheter guide wire using the shape memory alloy is steerable, it is difficult to form the end portion of the wire into a desired shape, because the catheter guide wire has the elasticity. Accordingly, it is necessary clinically to store a plurality of catheter guide wires having different end shapes which are called, for example, a J-shape type, an angular type, and others. However, if it is possible to readily plastically bend, deform, or work the end of the catheter guide wire into a desired shape, a single catheter guide wire can be adapted for various conditions of the catheter guide wire end shape.

Further, since the catheter guide wire using the shape memory alloy has the pseudo elasticity, it is readily elastically deformed by any force applied to the guide wire. Therefore, transmission of the force is insufficient through the catheter guide wire to the end portion from a portion away from the end portion, so that insertion force and/or rotating force applied to the catheter guide wire is hardly transmitted to the end portion. This means the guide wire does not have a good steerability.

SUMMARY OF THE INVENTION

Considering the above-mentioned problems, it is an object of the present invention to provide a catheter guide wire and a solid core wire for use in the catheter core wire which are readily plastically deformed at its end portion into a desired shape.

It is another object of the present invention to provide a catheter guide wire and a solid core wire for use in the catheter core wire which has rigidity or elasticity at the other portion extending from the end portion of the wire so as to improve the steerability of the wire.

The present invention is applicable to a solid core wire for use in a catheter guide wire used together with a catheter. The solid core wire comprises an end portion and the remaining portion extending therefrom. According to the present invention, at least the end portion is made of Ti-Ni alloy and has pseudo elasticity at a temperature about 37° C. and exhibits plasticity at a temperature below about 80° C.

In an aspect, the Ti-Ni alloy consists essentially of 45.0–51.0 at. % (atomic percent) Ni, 0.5–5.0 at. % Fe and the balance Ti. The end portion of the Ti-Ni alloy is a portion heat-treated at a temperature of 400°–500° C. after cold working into the core wire. The remaining portion may be made of a metallic alloy having with no elasticity pseudo elasticity.

In another aspect, the solid core wire is made of an alloy which consists essentially of 50.3–52.0 at. % Ni and the balance Ti. The end portion is heat-treated at a temperature of 700° C. or higher after cold working into the core wire. The remaining portion may be a portion heat-treated at a temperature lower than 400° C. after cold working into the core wire, the remaining portion having elasticity without pseudo elasticity.

In a further aspect, a solid core wire is made of a shape memory alloy, with the end portion having pseudo elasticity at a temperature about 37° C., the remaining portion having elasticity with no pseudo elasticity. The solid core wire comprises a discrete wire which is made of an alloy which comprises 50.3–52.0 at. % Ni and the balance Ti. The end portion is a portion heat-treated at a temperature of 400°–500° C. after cold working into the core wire. The remaining portion is heat-treated at a temperature lower than 400° C. after cold working into the core wire.

In another aspect, the core wire may further comprises a coating of an inorganic material which coats the discrete wire at the remaining portion. The coating is made of one selected from a group of nickel, stainless steel, silicon carbide and titanium nitride. The coating may be made of a metal alloy clad onto the discrete wire.

In a further aspect, a catheter guide wire is obtained which comprises the solid core wire and a synthetic resin jacket covering the core wire.

DESCRIPTION OF PREFERRED EMBODIMENTS

Figure 1:
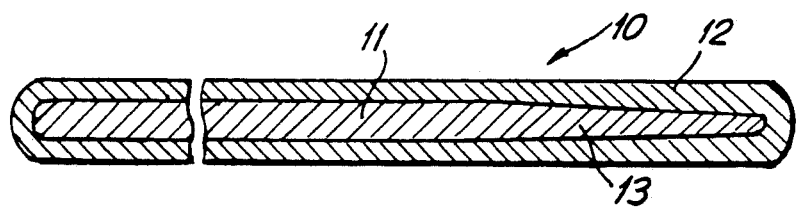
FIG. 1 is an enlarged sectional view of a catheter guide wire according to an embodiment of the present invention, with an intermittent portion being omitted.

Referring to FIG. 1, a catheter guide wire 10 according to an embodiment has a length of, for example, 1,800 mm and a diameter of, for example, 0.36 mm and comprises a solid core wire 11 and an outer jacket 12 covering the core wire 11.

The core wire 11 has an end portion 13 which is tapered. In an example, the core wire has a length of about 1,800 mm and a diameter of 0.25 mm. The end portion has a length of 120 mm and the tapered end of the end portion has a diameter of 0.06 mm.

Materials and properties of the core wire 11 will later be described.

The jacket 12 is in close contact with the core wire 11 and has an outer diameter constant along the longitudinal direction. Opposite ends of the jacket 12 are formed round.

The jacket 12 is made of any one of synthetic resins such as polyethylene, polyvinyl chloride, polyester, polypropylene, polyamide, polyurethane, polystyrene, fluoride resin, silicone rubber, and other elastomers.

Powder of Ba, W, Bi, Pb and/or other x-ray sensitive elements or chemical compounds containing them may be mixed and distributed in the synthetic resin layer of the jacket 12. In the case, it is possible to observe the catheter guide wire inserted in the blood vessels by use of a radioscopy.

An outer surface of the jacket 12 may be coated with an anticoagulant such as heparin, urokinase, and the like, or an antithrombin such as silicone rubber, block copolymer of urethane and silicone hydroxyethyl methacrylate styrene copolymer and the like.

An outer surface of the jacket 12 may be coated with a lubricant of water soluble high molecular compounds or their derivatives, for example, silicone oil so as to reduce the surface friction of the catheter guide wire.

Now, materials and properties of the solid core wire 11 will be described below.

In an embodiment of the present invention, the solid core wire 11 is made of Ti-Ni alloy having a pseudo elasticity at a temperature about 37° C. and a plasticity at a temperature below 80° C. An example of Ti-Ni alloy having such properties consists essentially of 45.0–51.0 at. % Ni, 0.5–5.0 at. % Fe, and the balance Ti, as demonstrated in EXAMPLE 1 below.

EXAMPLE 1

Sample Ti-Ni and Ti-Ni-Fe alloys 1-11 shown in Table 1 were prepared by use of a vacuum induction melting method.

TABLE 1

| Sample No. | | Ingredients (atomic percent) | | | Hot Work-ability | Cold Workability |
|---|---|---|---|---|---|---|
| | | Ti | Ni | Fe | | |
| Conventional | 1 | 50 | 51 | — | Good | Difficult |
| Comparative | 2 | 50 | 49.75 | 0.25 | Good | Good |
| Invention | 3 | 50 | 49.5 | 0.5 | Good | Good |
| | 4 | 50 | 48.5 | 1.5 | Good | Good |
| | 5 | 50 | 47 | 3 | Good | Good |
| | 6 | 40 | 45 | 5 | Good | Difficult |
| Comparative | 7 | 40 | 43 | 7 | Difficult | Impossible |

TABLE 1-continued

| Sample No. | | Ingredients (atomic percent) | | | Hot Work-ability | Cold Workability |
|---|---|---|---|---|---|---|
| | | Ti | Ni | Fe | | |
| | 8 | 50 | 40 | 10 | Difficult | Impossible |
| Invention | 9 | 48.5 | 48.5 | 3 | Good | Difficult |
| | 10 | 49 | 49 | 2 | Good | Good |
| | 11 | 49 | 51 | 1 | Good | Difficult |

Alternatively, an arc melting method, an electron beam melting method, or a powder metallurgy can be used.

Sample alloy 1 is a conventional Ti-Ni alloy without Fe. Sample alloys 2, 7 and 8 are comparative samples which are Ti-Ni-Fe alloys but are improper for the desired properties as will later be understood.

Each of the sample alloys 1–11 was solution treated at a temperature of 900°–1,000° C., hot forged at 900° C., cold drawn to have a diameter of 0.7 mm, and then annealed at 900° C. Thus, a wire of 0.5 mm diameter was produced.

WORKABILITY TEST

In the course of the hot and cold working processes, the hot workability and the cold workability were observed and the observed result is shown in Table 1.

With respect to the hot workability, sample aloys 1-6, 9, 10 and 11 were good but it was difficult to hot work comparative sample alloys 7 and 8.

With respect to the cold working, sample alloys 2-5 and 10 were good. Sample alloys 1, 6, 9 and 11 were difficult but could be cold worked. Sample alloys 7 and 8 could not be cold worked.

PSEUDO ELASTICITY TEST

The produced wires of each sample alloy having the diameter of 0.5 mm were heat treated or annealed at 900° C., 700° C., 600° C., 500° C., 400° C., and 300° C., respectively, for one hour. Thereafter, the heat-treated wires were subjected to a tensile strength test (the maximum strain of 3%) at the room temperature (20° C.) and the body temperature (37° C.). As a result, stress-strain curves of the sample alloy wires were obtained at the different temperatures. Sample alloys 7 and 8 were not tested because wires of the alloys were not obtained by the cold working.

It was noted from the test that the pseudo elasticity exhibiting yield point was not almost observed in all of the sample alloys 1-6, 9, 10 and 11 when they were not heat treated and even when they were heat treated at any temperaure below 400° C. However, they exhibited the pseudo elasticity having a clear yield point when they were heat treated at a temperature of 400°-500° C. when they were heat treated at a temperature of 600° C. or more, they exhibited the pseudo elasticity but they deteriorated after repetition of the tensile test.

Figure 2:
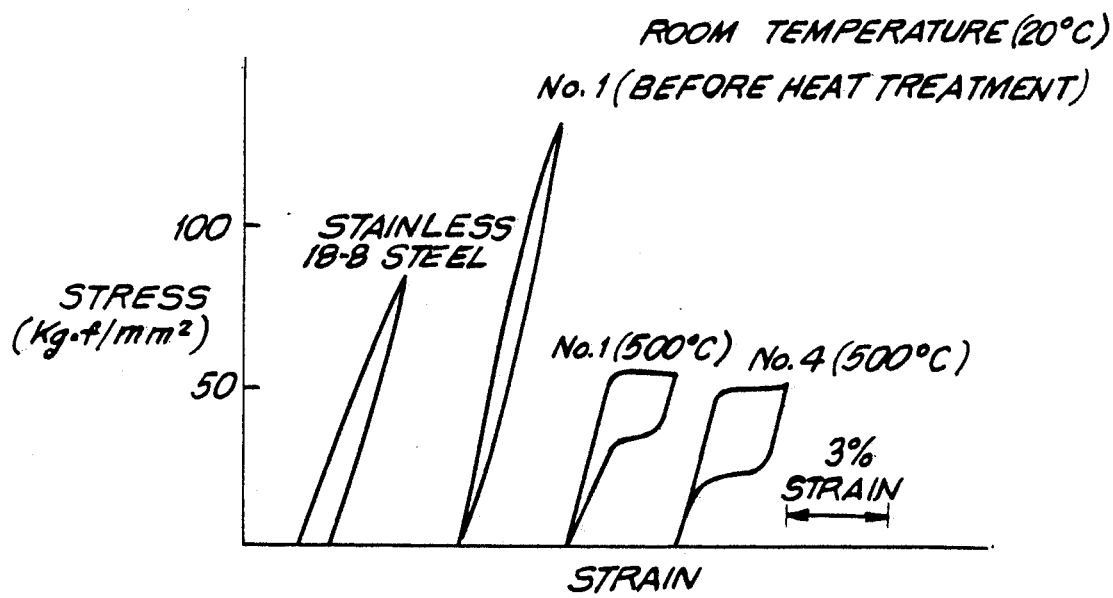
FIG. 2 is a view illustrating various stress-strain curves of sample wires in EXAMPLE 1 at 20° C.

In FIG. 2, stress-strain curves No. 1 (500° C.) and No. 4 (500° C.) at the room temperature are shown as to sample alloys 1 and 4 heat-treated at 500° C., respectively. For comparison with these, FIG. 2 also shows the stress-strain curves at the room temperature of known 18-8 stainless steel and the sample alloy 1 before the heat treating. It is found out from FIG. 2 that the sample alloys 1 and 4 heat-treated at 500° C. have the pseudo elasticity.

Table 2 shows stress for 3% strain at 37° C. of sample alloys 1-11 heat-treated at various temperatures.

TABLE 2

| Sample No. Heat Treatment | | Stress for 3% tensile strain (at 37° C.) (kg · f/mm²) | | | | | | |
| --- | --- | --- | --- | --- | --- | --- | --- | --- |
| | | Non | 300° C. | 400° C. | 500° C. | 600° C. | 700° C. | 900° C. |
| Conventional | 1 | 155 | 120 | 60 | 51 | 32 | 30 | 25 |
| Comparative | 2 | 160 | 130 | 65 | 50 | 28 | 30 | 35 |
| Invention | 3 | 170 | 130 | 55 | 50 | 30 | 29 | 30 |
| | 4 | 150 | 140 | 58 | 41 | 27 | 25 | 30 |
| | 5 | 140 | 130 | 58 | 43 | 30 | 28 | 28 |
| | 6 | 160 | 140 | 60 | 50 | 30 | 27 | 29 |
| Comparative | 7 | — | — | — | — | — | — | — |
| | 8 | — | — | — | — | — | — | — |
| Invention | 9 | 150 | 120 | 60 | 49 | 33 | 27 | 30 |
| | 10 | 180 | 140 | 59 | 50 | 35 | 25 | 26 |
| | 11 | 183 | 125 | 57 | 50 | 29 | 29 | 27 |

PLASTICITY TEST

The 500° C. heat-treated wires of sample alloys 1–6, 9, 10 and 11 were subjected to a plasticity test where each wire was bent by an angle of 90° at a temperature of 37° C. A residual strain of each sample wire was measured after removal of the bending stress and after heating each sample wire at 80° C. The measured data were shown in Table 3.

TABLE 3

| Sample No. | | Residual Strain (%) after bending by 90° C. angle (37° C.) | Residual Strain (%) after heating at 80° C. |
| --- | --- | --- | --- |
| Conventional | 1 | Very little | 0% |
| Comparative | 2 | Very little | 0% |
| Invention | 3 | about 50% | about 10% |
| | 4 | 100% | 90% or more |
| | 5 | 100% | 90% or more |
| | 6 | 100% (but tend to be broken) | 90% or more |
| Comparative | 7 | — | — |
| | 8 | — | — |
| Invention | 9 | 100% (but tend to be broken) | 90% or more |
| | 10 | 100% | 90% or more |
| | 11 | 100% | 90% or more |

In sample alloy 1, the initial shape before bending was almost restored at a moment when the bending stress was removed but a residual strain was slightly observed. That is, it is impossible to plastically deform the sample alloy 1 by application of stress. When the alloy was heated at 80° C., the slight residual strain vanished. In order to form the wire of sample alloy 1 into a fixed shape, it was necessary to heat treat the wire restrained in the shape at a temperature of 400°–500° C.

Although sample alloy 2 contains 0.25 at. % Fe, the residual strain was not almost observed after removal of the bending stress.

Sample alloy 3 containing 0.5 at % Fe exhibited the residual strain of about 50% after removal of the bending stress and about 10% even after heating at 80° C.

In any one of sample alloys 4–6, 9, 10, and 11, the residual strain was 100% after removal of the bending stress and was about 90% or more even after heating at 80° C.

Therefore, the sample alloys 3–6, 9, 10 and 11 can be drastically deformed by application of stress. Further, it was confirmed that the residual strain of 90% or more was maintained at 80° C. This means that a desired shape given to the wire is maintained even when it is dipped in hot water about 80° C. which is often used as a cleaning agent in use of the catheter guide wire.

The 500° C. heat-treated wire of sample alloy 5 was subjected to a tensile test to obtain stress-strain curves at 20° C., 40° C., 60° C., and 80° C. The obtained curves are shown in FIG. 3.

Figure 3:
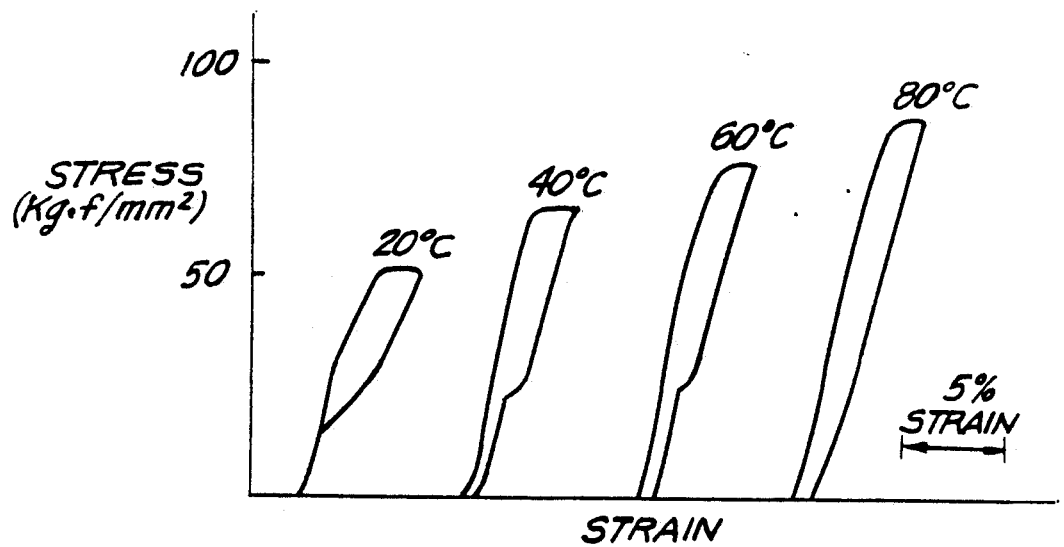
FIG. 3 is a view illustrating stress-strain curves of a 500° C. heat-treated wire at different temperatures.

FIG. 3 shows that the strain remains after removal of stress at 40° C. This means that a bent shape of 90° angle can be provided to the wire at 40° C. Further, it is noted from curves at 60° C. and 80° C. that the plastical deformation can stably be obtained at 60° C. and 80° C.

It is understood from EXAMPLE 1 that a solid core wire having the pseudo elasticity at 37° C. and the plasticity below 80° C. can be obtained by use of the alloy comprising 45.0–51.0 at. % Ni, 0.5–5.0 at. % Fe, and the balance Ti.

Returning to FIG. 1, the solid core wire 11 is not necessary to have the plasticity along the whole length. Usually, the end portion 13 is desired to be deformed into a shape such as j-shape. Therefore, the end portion 13 may only be made of the above-mentioned Ti-Ni-Fe alloy. The remaining portion of the solid core wire 11 may be made of a conventional Ti-Ni alloy. An example will be demonstrated below.

EXAMPLE 2

Wires of sample alloys 1 and 4 in EXAMPLE 1 were made with a diameter of 0.7 mm. Both of wires were brought into contact with each other at their ends and were fixedly jointed to form a single complex wire by welding the contacted ends. The complex wire was annealed at 900° C. and worked to have a diameter of 0.5 mm, and then, was heat treated at 400° C. for one hour. Thereafter, the portion of sample alloy 1 and the remaining portion of sample alloy 4 were subjected to a plasticity test similar to that in EXAMPLE 1. As a result, it was confirmed that the portion of sample alloy 1 and the remaining portion of sample alloy 4 had residual strains similar to sample alloys 1 and 4 in Table 3.

Therefore, it is possible to make a solid core wire having an end portion which has pseudo elasticity at a temperature about 37° C. and plasticity at a temperature below 80° C. The remaining portion has pseudo elasticity at a temperature about 37° C. but have no plasticity.

Alternatively, the remaining portion can be made of a conventional 18-8 stainless steel or a piano wire. In that case, the joint portion of the end portion and the remaining portion should be mechanically restrained by, for example, cauking or press-deformation so as to insure a high mechanical connecting strength.

It is possible to joint the above-mentioned complex wire with the 18-8 stainless steel or the piano wire to make a long wire. At that case, the end portion should be of the Ti-Ni-Fe alloy wire and the remaining portion comprises the Ti-Ni alloy wire and the stainless steel or the piano wire.

Ti-Ni alloy containing no Fe can have pseudo elasticity at a temperature about 37° C. and plasticity at a temperature below 80° C., by adjusting the amounts of Ti and Ni and the heat-treating temperature. The Ti-Ni alloy having such properties consists essentially of 50.3-52.0 at. % Ni and the balance Ti. When the Ti-Ni alloy containing Ni of 50.0 at. % or more is heat-treated at a temperature of 700° C. or more, it exhibits pseudo elasticity at a temperature about 37° C. and plasticity at a temperature below 80° C. The plasticity is not obtained at Ni amount less than 50.3 at. % by the heat treatment at 700° C. The alloy containing Ni more than 52.0 at. % is deteriorate in workability and is improper for the practical use. An example is demonstrated in EXAMPLE 3 below.

EXAMPLE 3

A wire of sample alloy 1 in Table 1 was prepared by a melting method, a hot forging, a hot rolling, a cold drawing similar to those in EXAMPLE 1. The cold drawn wire had a diameter of 0.5 mm. Then, the drawn wire was subjected to a straightening at 300° C. for five minutes.

A sample piece of 2 m was cut out from the wire and an end portion (50 mm) of the sample piece was dipped into a salt bath which was maintained at 700° C. for two minutes, thereafter rapidly cooled.

Figure 4:
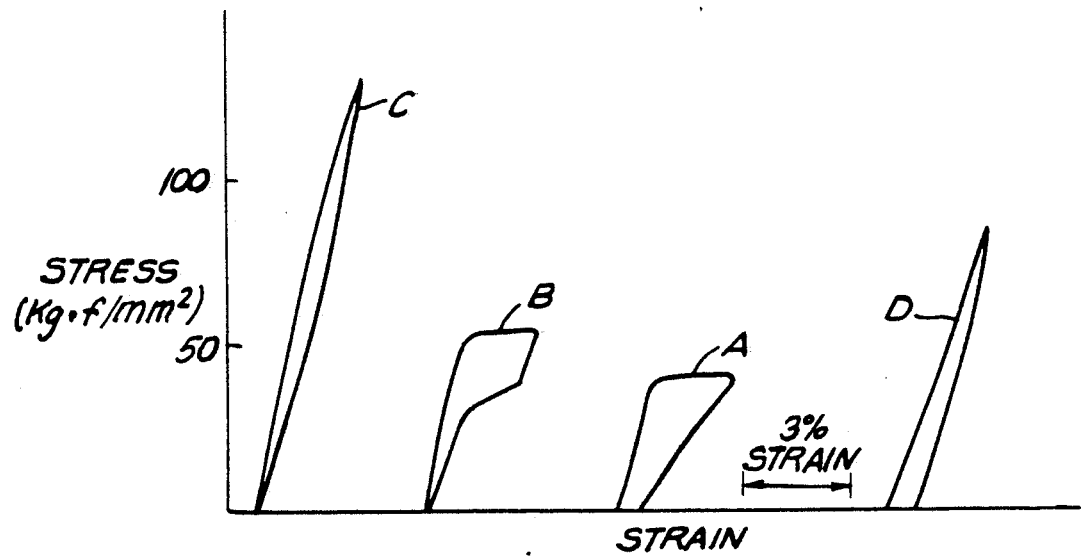
FIG. 4 is a view illustrating stress-strain curves of sample wires in EXAMPLES 2 and 3.

Then, the end portion was subjected to a tensile test at 37° C. and obtained a stress-strain curve. The resultant stress-strain curve is shown at A in FIG. 4.

It is noted from curve A that yield occurs by about 1% strain without plasticity. Therefore, the end portion has the pseudo elasticity. However, when strain of 3% or more are applied, a high residual strain is observed. Therefore, the end portion can be plastically deformed.

Returning to FIG. 1, the end portion 13 of solid core wire 11 has the pseudo elasticity at 37° C. while the remaining portion having rigidity or elasticity in another embodiment of the present invention. Some examples are shown below.

EXAMPLE 4

A sample piece of 2 m was cut out from the wire prepared in EXAMPLE 3 and an end portion (50 mm) of the sample piece was dipped into a salt bath which was maintained at 400° C. for ten minutes, thereafter rapidly cooled.

Then, the 400° C. heat-treated end portion and the non-treated remaining portion were subjected to a tensile test at 37° C. and obtained stress-strain curves. The resultant stress-strain curves are shown at B and C, respectively, in FIG. 4. A stress-strain curve of 18-8 stainless steel wire is also shown at D in the figure.

It is noted from curve B that the end portion has a clear yield point at 1% strain for 60 kg.f/mm² stress. Further, strain of 3% completely vanishes by removal of stress. Therefore, the end portion has the pseudo elasticity.

On the other hand, the remaining portion has the complete elasticity for stress higher than 100 kg.f/mm² as shown at curve C which is superior to 18-8 stainless steel wire of curve D. The stainless steel has 3% strain for 100 kg.f/mm² and has a residual strain after removal of the stress as shown at curve D.

The pseudo elasticity is obtained by the heat treatment at a temperature of 400°-500° C. as already described in EXAMPLE 1.

In a solid core wire of a shape memory alloy having the pseudo elasticity, the rigidity can also be given to the remaining portion by covering it with inorganic coating as described in the following examples.

EXAMPLE 5

A wire having a diameter of 0.5 mm was worked from an 51 at % Ni-49 at % Ti alloy in the similar manner in EXAMPLE 4. The worked wire was heat treated at 400° C. for ten minutes.

The heat treated wire was subjected to a tensile test at 37° C. to obtain a stress-strain curve with a maximum strain of 3%. The resultant curve is equal to the curve B in FIG. 4 because the alloy has the same composition and is subjected to the same heat treatment in EXAMPLE 4. The resultant curve is shown at B in FIG. 5. The stress-strain curve of 18-8 stainless steel is also shown at D in FIG. 5.

The heat treated wire is superior to the 18-8 stainless steel in the elasticity and the flexibility.

A plurality of samples cut out from the heat treated wire were coated with Ni by the electroplating, stainless steel (SS) by evaporating, silicon carbide (SiC) by spattering, and titanium nitride (TiN) by spattering. The coating had a thickness of 25-50 μm.

Figure 5:
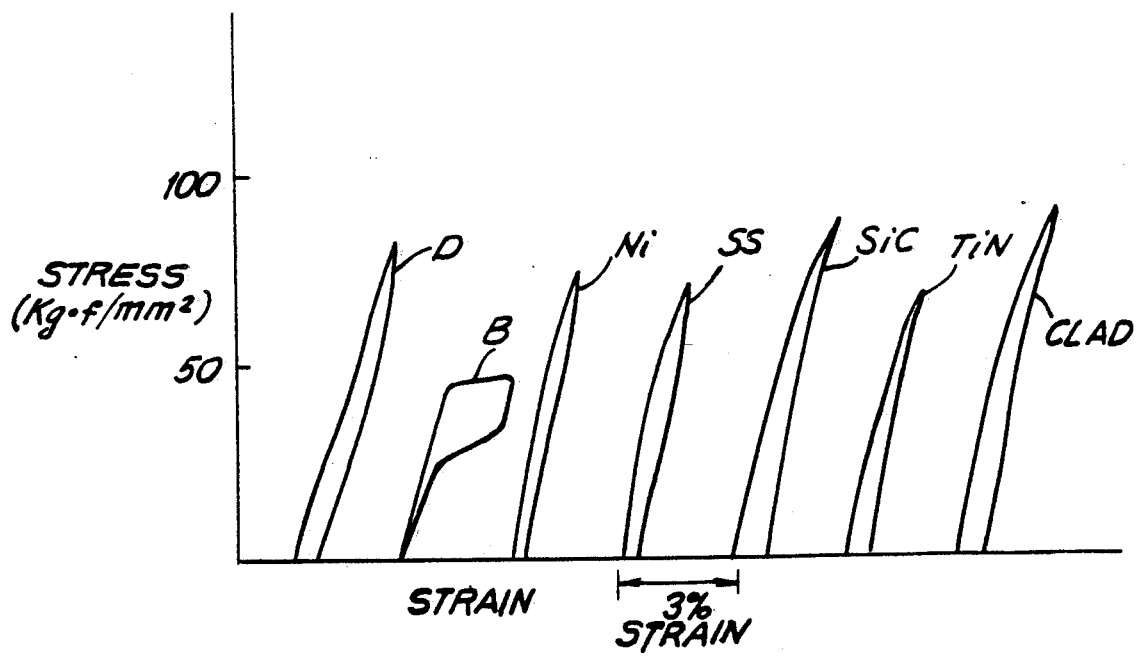
FIG. 5 is a view illustrating stress-strain curves of sample wires in EXAMPLES 4 and 5.

Stress-strain curves at 37° C. of the coated wires were measured and are shown with references of Ni, SS, SiC, and TiN, respectively, in FIG. 5. It is noted from those stress-strain curves that each of the coated sample wires has a small residual strain and a high rigidity similar to the stainless steel wire.

Each of the coated sample wires was subjected to removal of the coating at the end portion over a length of 50 mm by a chemical treatment using aqua regia or by mechanical grinding and the end portion of Ti-Ni alloy was exposed.

The end portion exposed is subjected to the tensile test to obtain a stress-strain curve with a maximum strain of 3%. The curve was confirmed equal to curve B in FIG. 5.

Thus, the solid core wire is obtained with an end portion having the pseudo elasticity and the remaining portion having the high elasticity.

The coating can be replaced by cladding as described in the following example.

EXAMPLE 6

Sample alloy 1 in EXAMPLE 1 was worked to form a wire having a diameter of 5.0 mm. The worked wire was inserted in a stainless steel tube having an inner diameter of 5.1 mm and an outer diameter of 6.0 mm to form a clad-type wire.

The clad-type wire was swaged or forged to have a reduced diameter of 0.7 mm and then, cold drawn to form a clad wire of a 0.5 mm diameter.

The clad wire was subjected to a heat treatment at 400° C. for ten minutes and to a tensile test at a temperature of 37° C. A resultant stress-strain curve is shown with a reference of CLAD in FIG. 5. It is noted form the resultant stress-strain curve CLAD that the heat-treated clad wire has high rigidity similar to curve D of the stainless steel wire.

Then, the stainless steel cladding was removed at an end portion over 50 mm by use of aqua regia to expose the end portion of the Ti-Ni alloy.

The end portion exposed was again subjected to a tesile test at a temperature of 37° C. and obtained a stress-strain curve similar to curve B in FIG. 5.

The end portion may be chemically treated by use of hydrofluoric acid to be tapered.

What is claimed is:

1. A length of solid core wire for use in a catheter guide wire, said core wire/catheter guide wire together having particular use with a catheter:

said length of core wire comprising an end portion and a remainder portion extending therefrom, said end portion comprising a Ni-Ti alloy characterized by pseudoelasticity at a temperature of about 37° C. and which exhibits plasticity at a temperature less than about 80° C., whereby said end portion can be readily deformed into a desired shape.

2. The solid core wire as claimed in claim 1, wherein said Ti-Ni alloy consists essentially of about 45.0 to 51.0 atomic percent Ni, about 0.5 to 5.0 atomic percent Fe and the balance Ti, and wherein said end portion is heat-treated at a temperature of about 400° to 500° C. following cold working of said alloy into said core wire in order to provide said pseudoelasticity and said plasticity.

3. The solid core wire as claimed in claim 2, wherein said remainder portion is made of metallic alloy exhibiting elasticity but no pseudoelasticity and which is joined in end-to-end relationship to said end portion and thereby provide a single wire thereof.

4. The solid core wire as claimed in claim 3, wherein said remainder portion is made of a Ni-Ti alloy comprised of about 51.0 atomic percent Ni and the balance Ti.

5. The solid core wire as claimed in claim 1, wherein said solid core wire is made of Ni-Ti alloy, said Ni-Ti alloy comprising about 50.3 to 52.0 atomic percent Ni and the balance Ti, and wherein said end portion is heat-treated at a temperature of about 700° C. or higher after cold working said alloy into said core wire and thereby provide it with said pseudoelasticity and said plasticity.

6. The solid cold wire as claimed in claim 5, wherein said remainder portion is heat-treated at a temperature lower than about 400° C. following cold working of the alloy into said core wire, whereby said remainder portion of said core wire exhibits elasticity but no pseudoelasticity.

7. A catheter guide wire comprising said solid core wire as defined in claim 1 and including a synthetic resin jacket covering said core wire.

8. A length of solid core wire for use in a catheter guide wire, said core wire/catheter guide wire together having particular use with a catheter, said length of core wire comprising and end portion and a remainder portion extending therefrom, wherein said core wire is made of a shape memory alloy, wherein said end portion exhibits pseudoelasticity at a temperature of about 37° C., and wherein said remainder portion exhibits elasticity but no pseudoelasticity.

9. A solid core wire as claimed in claim 8, wherein said solid core wire comprises a discrete wire made of an alloy consisting essentially of about 50.3 to 52.0 atomic percent Ni and the balance titanium, and wherein said end portion is heat treated at a temperature of about 400° to 500° C. after cold working said alloy into the core wire and thereby provide it with pseudoelasticity.

10. A solid core wire as claimed in claim 9, wherein said remainder portion is heat treated at a temperature less than 400° C. after cold working the alloy into the core wire and thereby provide it with elasticity and no pseudoelasticity.

11. The solid core wire as claimed in claim 8, wherein said core wire comprises a discrete wire made of an alloy consisting essentially of about 50.3 to 52.0 atomic percent Ni and the balance Ti, wherein said discrete core wire is heat-treated at a temperature of about 400° to 500° C., wherein said discrete wire is provided with coating of inorganic material at said remainder portion, and wherein said end portion exhibits pseudoelasticity and said remaining portion exhibits elasticity and no pseudoelasticity.

12. The discrete solid core wire as claimed in claim 11, wherein said coating is selected from the group consisting nickel, stainless steel, silicon carbon and titanium nitride.

13. The discrete core wire as claimed in claim 11, wherein said coating is made of a metal alloy clad onto said discrete wire.

14. A catheter guide wire comprising a solid core wire as in claim 8, including a synthetic resin jacket covering said core wire.

* * * * *